United States Patent [19]  
Buchegger et al.

[11] Patent Number: 4,486,098  
[45] Date of Patent: Dec. 4, 1984

[54] METHOD AND APPARATUS FOR TESTING THE ENDS OF CIGARETTES OR THE LIKE

[75] Inventors: Joachim Buchegger, Richmond; Andrej Radzio, Quinton, both of Va.

[73] Assignee: Hauni-Werke Körber & Co. KG, Hamburg, Fed. Rep. of Germany

[21] Appl. No.: 351,475

[22] Filed: Feb. 23, 1982

[51] Int. Cl.³ .................. G01N 21/55; B07C 5/342
[52] U.S. Cl. .................. 356/445; 209/536; 250/223 R; 356/448
[58] Field of Search .......... 356/445, 448, 237; 250/223 R; 209/536; 131/908, 910

[56] References Cited

U.S. PATENT DOCUMENTS

| | | | |
|---|---|---|---|
| 2,690,258 | 9/1954 | Cox | 250/223 R X |
| 3,557,374 | 1/1971 | Schmermund | 250/223 R X |
| 3,729,636 | 4/1973 | Merker | 209/536 X |
| 3,980,567 | 9/1976 | Benini | 250/223 R |
| 4,090,794 | 5/1978 | Benini | 356/445 |
| 4,124,803 | 11/1978 | Bowers | 356/448 X |
| 4,266,674 | 5/1981 | Bell et al. | 209/536 |
| 4,267,444 | 5/1981 | Bald | 209/536 X |
| 4,290,698 | 9/1981 | Milana | 356/448 X |

Primary Examiner—Vincent P. McGraw  
Attorney, Agent, or Firm—Peter K. Kontler

[57] ABSTRACT

Filter cigarettes which are grouped in the form of one or more rows on their way to the draping station or stations of a packing machine are transported sideways past a testing station between two testing units each of which has a discrete detector for each row of cigarettes in a group. Each detector has a source of light, a photoelectric transducer, and a bundle of fiber optics which convey light beams from the source against the respective end faces of cigarettes advancing between the two testing units and which convey reflected light to the respective transducer so that the latter generates signals denoting the characteristics, the presence or absence of cigarettes. Such signals are compared with a reference signal denoting the characteristics of satisfactory cigarettes, and the groups wherein one or more cigarettes have caused the generation of signals deviating excessively from the reference signal are expelled from the conveyor prior to reaching the first draping station of the packing machine. The extent of contamination by tobacco dust or the like of optical elements through which the light beams pass is monitored, and the signals which denote the extent of detected contamination are used to modify the signals denoting the characteristics of the tested cigarettes, to effect automatic cleaning of the optical elements and/or to arrest the packing machine.

23 Claims, 7 Drawing Figures

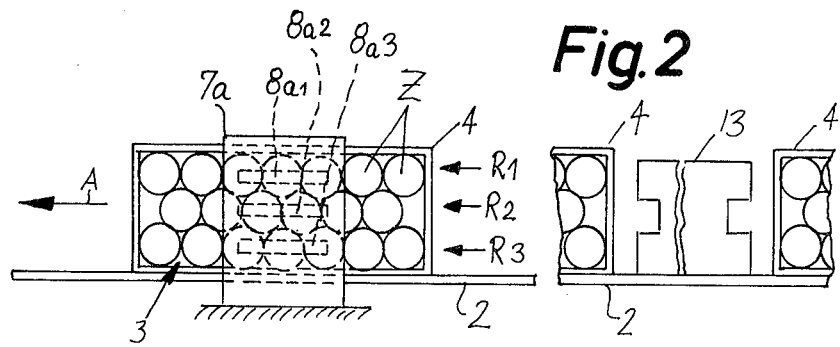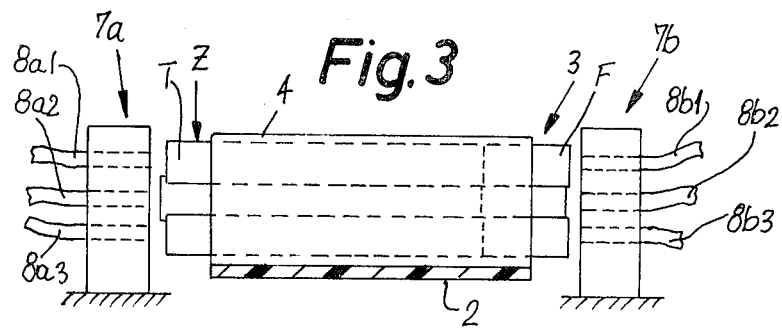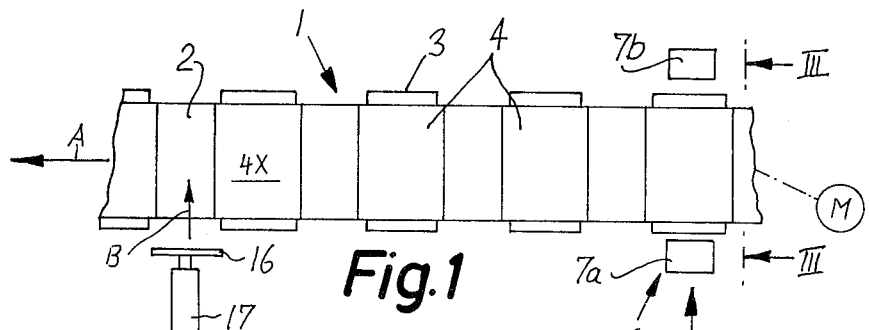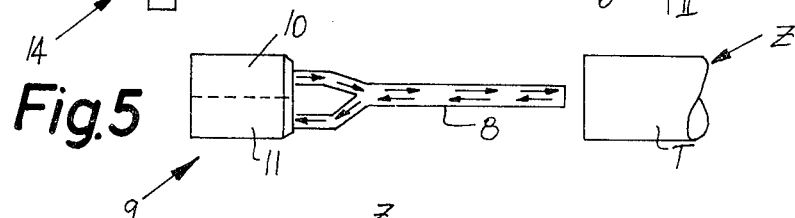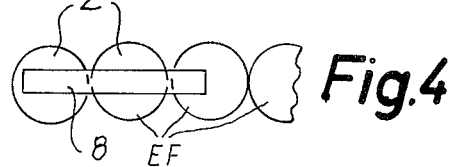

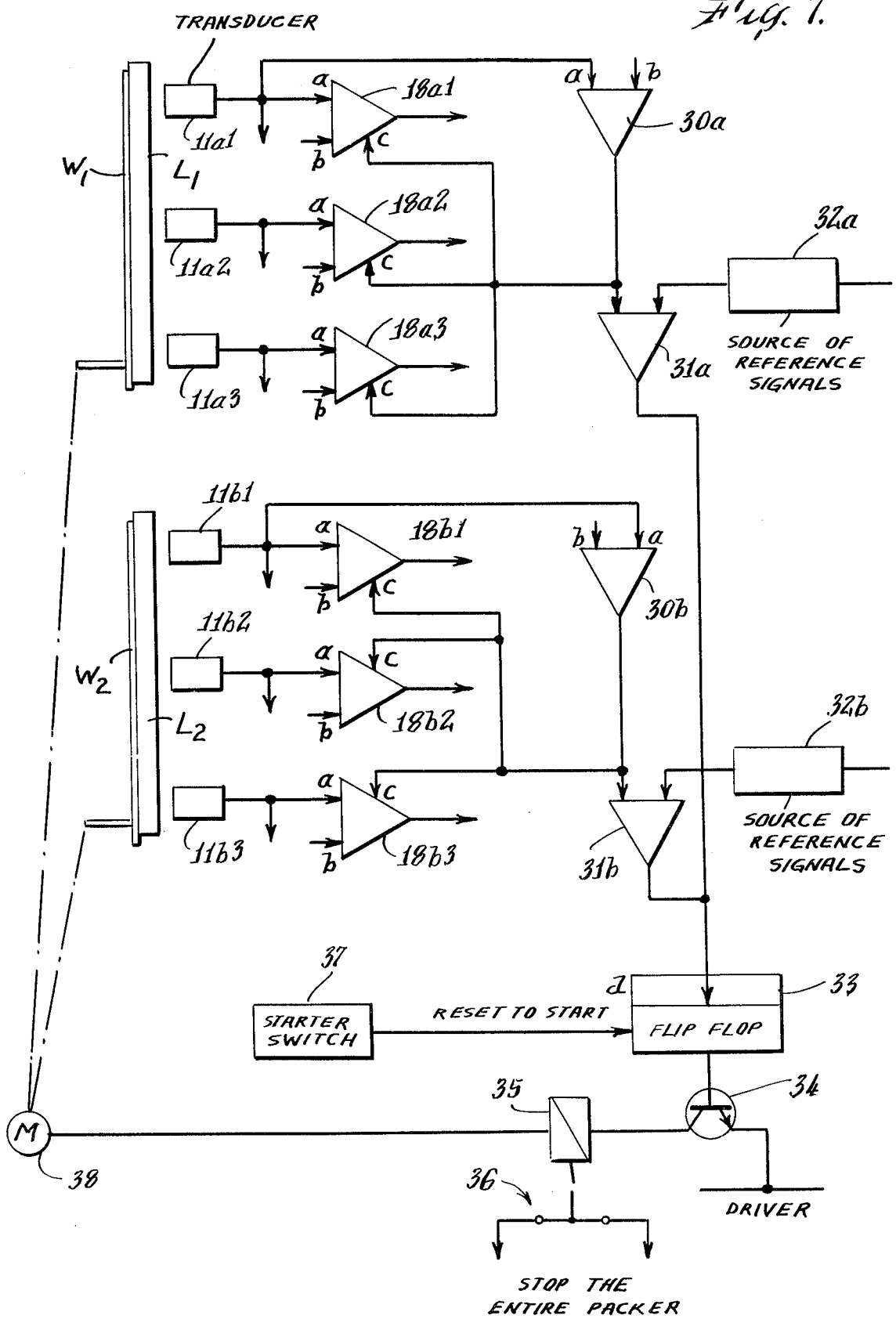

METHOD AND APPARATUS FOR TESTING THE ENDS OF CIGARETTES OR THE LIKE

BACKGROUND OF THE INVENTION

The present invention relates to testing apparatus and methods in general, and more particularly to improvements in methods and apparatus for testing cigarettes, cigars, cigarillos, cheroots, filter rod sections and analogous rod-shaped articles which constitute or form part of smokers' products. Still more particularly, the invention relates to improvements in methods and apparatus for simultaneous testing of groups or arrays of parallel rod-shaped articles.

It is well known to monitor the contents of partly finished or sealed packs containing groups of parallel cigarettes or other smokers' products, or to test groups of such products prior to introduction into packs or analogous containers. The purpose of testing is or can be manifold, i.e., to ascertain the presence or absence of a requisite number of products, to ascertain whether or not the products are properly arrayed, to ascertain whether or not the ends of the products are sufficiently or overly dense, to ascertain whether or not the ends of the products carry particles of foreign matter (e.g., fragments of tobacco shreds on filter plugs), whether or not the ends of the products are properly recessed and/or a combination of such parameters. For example, filter cigarettes which are about to be introduced into soft or hinge-lid packs are admitted into the magazine of a packing machine, arrayed in groups containing predetermined numbers of filter cigarettes (e.g., in arrays of twenty including a median row or layer of six filter cigarettes and two outer rows or layers of seven filter cigarettes each, with the articles of the median row staggered relative to those in the outer rows to constitute so-called quincunx formations), introduced into hollow mandrels, and confined in packs which are built around the mandrels. Prior to sealing of both ends of a freshly formed pack, the array of cigarettes is expelled from the respective mandrel to thereby strip the pack off the mandrel, whereupon the still open end of the pack is closed and sealed, e.g., by the application of a revenue stamp or label. Testing of arrays or groups of filter cigarettes normally takes place during transport of filled mandrels to the locus of application of the first or innermost envelope, e.g., a layer of metallic foil. During such transport, the tobacco-containing ends of filter cigarettes are accessible at one open end, and the filter plugs of the articles are accessible at the other open end of the mandrel. This enables suitable testing instrumentalities (such as photocells, movable pins or the like) which are adjacent to the path of movement of the mandrels to monitor the respective end portions of successive groups of filter cigarettes and to generate signals which are thereupon evaluated and processed to effect segregation of defective groups from satisfactory groups.

A drawback of presently known apparatus for the testing of groups of filter cigarettes or analogous rod-shaped articles of the tobacco processing industry is that they are overly complex, unreliable, too sensitive, not suited for testing beyond a certain frequency and/or too bulky for installation in the space which is available in or next to a making or processing machine in a cigarette manufacturing or like plant. Moreover, certain presently known testing apparatus are incapable of simultaneously monitoring two or more different characteristics of successive groups of products so that several apparatus must be installed in series in order to ascertain individual characteristics of successive groups which are caused to advance therealong.

German Offenlegungsschrift No. 28 13 866 discloses an apparatus which can be used for detection of loose ends and for detection of the absence of cigarettes in groups corresponding to those in a cigarette pack or the like. The apparatus employs a discrete bundle of fiber optics sensors for each and every article of a group. All of the bundles (i.e., normally twenty of them when the groups constitute customary arrays of twenty cigarettes each) can receive light from a common source. A drawback of such apparatus is the high number of bundles it must employ. This publication further discloses that the fiber optics of each bundle can include two sections one of which directs light against the ends of articles to be tested and the other of which receives reflected light. The arrangement may be such that one section of each bundle surrounds the other section or that the two sections form a pair of elongated parallel rectangles. In either event, a discrete bundle is needed for each and every article of a group to be tested. This means that, if the apparatus of this German publication were designed for simultaneous testing of both ends of each of a group of twenty arrayed plain cigarettes which are about to be packed, the apparatus would require a total of forty fiber bundles or, otherwise stated, twice as many fiber optics bundles as the number of plain cigarettes in a group. Such apparatus would necessitate the utilization of a highly complex evaluating circuit which would contribute significantly to the initial and maintenance cost as well as to proneness of the control system to malfunction.

German Offenlegungsschrift No. 22 36 218 discloses an apparatus for the testing of successive cigarettes of a layer or row of cigarettes which are transported sideways from a maker to a packing machine. The apparatus employs a so-called bifurcated or branched fiber optics bundle with a random mix of fibers adjacent to the path of one end of each of a series of successive cigarettes. One branch receives light from a suitable source and the other branch transmits light, which is reflected by successive cigarettes, to a photocell which transmits signals to a bridge circuit serving to evaluate the signals and to activate an ejector when the incoming signals denote the detection of defective cigarettes. If such apparatus were to be converted for the testing of groups of cigarettes in a packing machine, its random mix of fibers would have to be designed to assume a shape conforming to that of the ends of all cigarettes in a group and the groups would have to be arrested in positions of alignment with the random mix of fibers. This would entail a slowdown of the packing machine. Furthermore, it would be impossible to pinpoint the defective articles of a group and/or the general positions of defective articles, i.e., whether in an outer row or in a median row, so that the detection of defective articles would be of no help in attempting to localize or pinpoint the cause or causes of defects.

A drawback which is common to each of the aforediscussed prior apparatus is that the configuration of each bundle of optical fibers approximates or equals the shape of the end of an article which is to be tested. In most instances (such as in the apparatus of the German Offenlegungsschrift No. 22 36 218), the cross-sectional area of that end of the bundle which is adjacent to the path of cylindrical articles to be tested has a circular outline. The other German publication discloses the aforediscussed sections one of which surrounds the other and constitutes an annulus having an outer diameter matching or approximating that of the article to be tested, or two elongated parallel rectangular sections whose length matches or closely approximates the diameter of an article.

Another drawback which is common to heretofore known apparatus is that progressive contamination of lenses, mirrors and/or other optical elements which are used therein entails a continuous reduction of accuracy with which the apparatus ascertain the condition of the articles to be tested. Therefore, the machine employing the testing apparatus must be arrested at frequent intervals in order to remove from the optical elements tobacco dust and/or other contaminants which interfere with the generation of reliable signals and prevent the evaluating circuit or circuits from indicating the need for or from initiating corrective measures in immediate response to development of a malfunction which causes the production of unsatisfactory articles. In many instances, stoppage of the machine is not necessary at all, i.e., the contamination is not sufficiently pronounced to warrant an interruption of the operation and attendant huge losses in output.

OBJECTS AND SUMMARY OF THE INVENTION

An object of the invention is to provide a novel and improved apparatus which can monitor several characteristics of each of a series of rapidly advancing arrays or groups of cigarettes or analogous rod-shaped articles.

Another object of the invention is to provide an apparatus which can be installed in existing cigarette making, processing or like machines as a superior substitute for heretofore known testing apparatus.

A further object of the invention is to provide a novel and improved apparatus for testing groups consisting of one or more rows of filter cigarettes or the like in a packing machine.

An additional object of the invention is to provide the apparatus with novel and improved means for scanning the mandrels of a cigarette packing machine for the completeness, distribution and/or condition of their contents.

Another object of the invention is to provide the apparatus with novel and improved calibrating means to automatically ascertain the condition of its signal generating components at desired intervals.

Still another object of the invention is to provide the testing apparatus with novel and improved means for monitoring the condition of portions of successive groups of rod-shaped articles in a cigarette packing or like machine.

A further object of the invention is to provide novel and improved signal evaluating or processing means for use in an apparatus of the above outlined character.

A further object of the invention is to provide a novel and improved method of testing rows of parallel rod-shaped articles which constitute or form part of smokers' products.

An additional object of the invention is to provide a method which can be resorted to for testing of groups or arrays of rod-shaped articles which are about to be draped in metallic, plastic and/or paper blanks to constitute therewith packs of cigarettes or other smokers' products.

Another object of the invention is to provide a method which can be resorted to for simultaneous monitoring of both end faces of each of a series of successive rows or groups of rows of rod-shaped articles which constitute or form part of smokers' products, for example, to simultaneously monitor the exposed end faces of tobacco-containing sections and filter mouthpieces in filter cigarettes, cigars or cigarillos.

An additional object of the invention is to provide a method which is highly reliable, which allows for pinpointing and segregation of all such rows or groups of rows of rod-shaped articles wherein one or more articles are missing or defective, and which renders it possible to test rows or groups of rows of articles at the rate at which such articles are transported into and in a modern high-speed packing machine for cigarettes or other rod-shaped smokers' products.

Still another object of the invention is to provide the testing apparatus with novel and improved means for automatic compensation of progressive contamination of certain of its components and/or for automatic stoppage of the machine in which the apparatus is used when the contamination progresses to such an extent that further operation of the apparatus without removal of accumulated contaminants is not warranted.

An additional object of the invention is to provide the apparatus with novel and improved means for arresting the machine which turns out or processes the articles to be tested only when the extent of contamination of certain components of the apparatus warrants such stoppage.

Another object of the invention is to provide the apparatus with novel and improved means for removing contaminants from the optical element or elements which are used therein to focus radiation upon selected portions of articles to be tested or to direct reflected radiation to associated transducers or the like.

An additional object of the invention is to provide a novel and improved evaluating circuit which embodies the aforediscussed compensating means and which is capable of automatically arresting the article producing or processing machine when warranted in view of the contamination of certain components of the apparatus.

In accordance with a feature of the present invention, the testing means of the apparatus employs a single detector for each row of articles in a group, and each detector of the improved apparatus employs a single bundle of optical fibers (e.g., randomly distributed light-admitting and light-receiving fibers) for the respective layer or row of articles in a group of articles to be tested. Thus, if a group contains a single row of parallel articles, the testing means can comprise a single detector with a single bundle of optical fibers and, if a group contains two or more parallel rows of articles, the number of detectors and bundles is n wherein n equals the number of rows in a group. Moreover, the thickness of each bundle (as measured at right angles to the direction of transport of articles past the testing means) is or can be only a small and, in fact, a minute fraction of the diameter of an article. As a rule, the thickness of a single bundle or fiber sensor need not appreciably exceed a small fraction of the radius of an article. In most instances, the neighboring articles of a row of articles in a group which is ready to be packed abut against each other and thereby undergo at least some deformation so that the end faces of their wrappers are at least slightly out of round. As a rule, the thickness of the single fiber sensor need not exceed the width of the surfaces of contact between the neighboring articles of a row. This ensures that the light-admitting fibers invariably direct light against the end faces of passing articles and the light-receiving fibers invariably receive reflected light (if any) in spite of the fact that the thickness of the sensor or sensors is less than the diameter of an article and that the articles are at least substantially round. Otherwise stated, a feature of the invention can be said to reside in that the sensor or sensors of the detector or detectors are positioned or distributed in such a way that, owing to slight deformation of the neighboring articles in a row, each sensor can uninterruptedly scan a row of discrete substantially rod-shaped articles with attendant simplification of the evaluating or processing circuit which receives signals directly from the light-receiving fibers, or from a photocell or another suitable transducer which receives light from certain optical fibers.

The source of light may include one or more light emitting diodes. As is well known, such light sources exhibit the advantage that they can be pulsated at a high frequency so that they are turned on only while a row of articles advances past a sensor and that they are turned off immediately when the row has advanced beyond the respective sensor or when a row is assumed to have advanced beyond the associated sensor. This allows for highly accurate timing of the intervals of sensing with attendant detection of the presence or absence of requisite numbers of articles in each row of the tested group of articles.

The method of the present invention is resorted to for testing cigarettes or analogous rod-shaped articles which constitute or form part of smokers' products. The method comprises the steps of transporting successive groups—each of which consists of at least one row of parallel articles—sideways along a predetermined (preferably endless) path, testing successive articles of successive rows in a predetermined portion of the path including establishing a light source (e.g., a diode which emits infrared light), directing from the light source a plurality of light beams along discrete optical paths (such paths are preferably established by resort to glass fibers) against one end face of each article of a row in the aforementioned portion of the path (i.e., at a testing station) so that the one end face reflects the light beams and the extent of such reflection is indicative of the condition, presence or absence of articles and utilizing the reflected light to generate signals (e.g., by resort to a photoelectronic transducer) denoting the extent of light reflection, and thereupon processing the thus obtained signals (preferably for the purpose of expelling from a second portion of the path all such groups wherein at least one article (this includes missing or absent articles) has caused the generation of a signal indicating that the respective row is incomplete or contains at least one unsatisfactory article).

The processing step can comprise comparing the signals with a reference signal denoting the desired light reflectivity of the end faces of articles, and ejecting from the path those rows (preferably those groups) wherein the testing of articles has resulted in the generation of signals deviating excessively from the reference signal.

The method preferably further comprises the step of simultaneously testing the second end face of each successive article in each row, preferably (but not necessarily) in the aforementioned predetermined portion of the path.

If each group contains several rows of parallel articles, the testing step includes testing the end faces of all articles in a group at one side of the path during transport of groups along the aforementioned predetermined portion of the path.

The method can further comprise the steps of monitoring the quantity of contaminants (such as tobacco dust) which accumulate in the path of directed or reflected light beams of and adjusting the signals so as to account for the extent of contamination of such path or paths. An additional step may include terminating the transporting, testing, article making and/or article processing step when the contamination of the aforementioned path or paths has progressed to an extent which warrants an interruption of the operation e.g., because the signals cease to be truly representative of the condition of tested portions of the articles. Still another step may comprise automatically removing contaminants from the path or paths of light when the contamination reaches a maximum permissible value.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a plan view of a portion of a conveyor for blocks or cigarettes and of the cigarette testing and cigarette segregating stations;

FIG. 2 is an enlarged front elevational view of a detail as seen in the direction of arrow II in FIG. 1;

FIG. 3 is an enlarged transverse vertical sectional view as seen in the direction of arrows from the line III—III of FIG. 1;

FIG. 4 illustrates a detail of the testing means, showing a sensor in the process of monitoring the ends of a row of aligned smokers' products;

FIG. 5 is a schematic side elevational view of a detector in one of the two testing units;

FIG. 7 shows a portion of the circuit which is illustrated in FIG. 6 and an arrangement which can compensate for progressive contamination of certain components of the improved apparatus.

DESCRIPTION OF THE PREFERRED EMBODIMENTS

Figure 6:
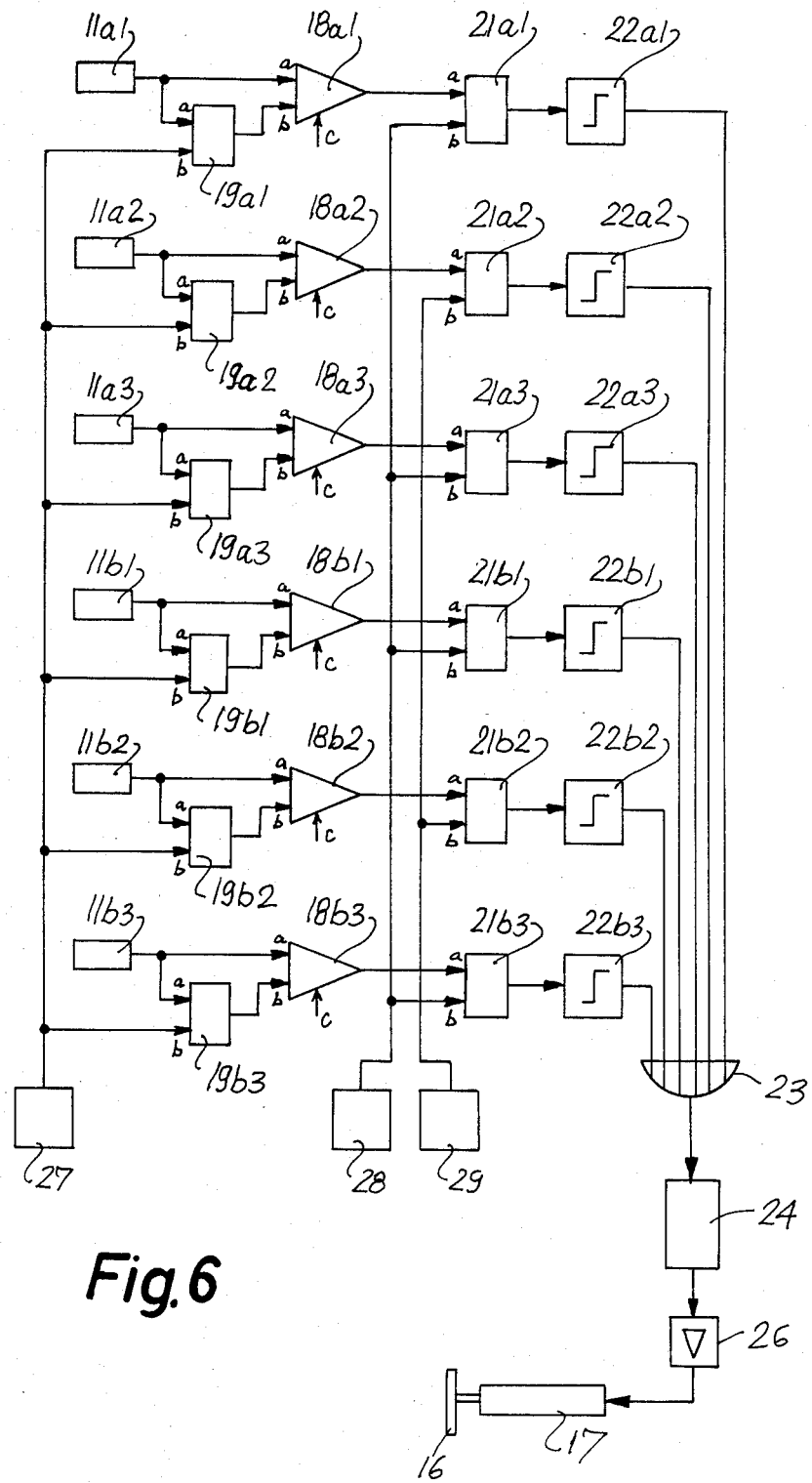
FIG. 6 is a circuit diagram of the signal processing and evaluating means in the apparatus which embodies the structure of FIGS. 1 to 5.

Referring first to FIGS. 1 to 3, there is shown a conveyor 1 including an endless toothed belt 2 (the teeth of the belt 2 are not specifically shown) which carries spaced-apart receptacles 4 for groups or arrays 3 of twenty filter cigarettes Z. Each group or array 3 includes two parallel outer rows R1 and R3 of seven parallel cigarettes Z and a median row R2 of six cigarettes Z which are staggered with reference to the cigarettes of the outer rows R1 and R3 in a manner best shown in FIG. 2 and customary in cigarette packs containing groups of twenty cigarettes Each cigarette Z comprises a tobacco-containing section T and a filter mouthpiece F.

The conveyor 1 transports successive groups or arrays 3 of cigarettes Z past a testing station 6 which accommodates a testing means including two testing units or devices 7a and 7b disposed opposite each other and at the opposite sides of the path of movement of the belt 2. Each of the testing units 7a and 7b contains three sensors which are shown in FIGS. 2 and 3. The sensors of the testing unit 7a are respectively shown at 8a1, 8a2 and 8a3, and the sensors of the testing unit 7b are respectively shown at 8b1, 8b2 and 8b3. Each of the sensors 8a1 to 8b3 comprises a large number of elongated optical fibers.

Each sensor forms part of a discrete detector 9 of the type shown in FIG. 5. The detector 9 of FIG. 5 comprises a light source 10 (e.g., a light-emitting diode) and a photosensitive transducer 11. One half of optical fibers forming the sensor 8 shown in FIG. 5 receive light from the source 10, and the other half of such fibers transmit reflected light (if any) to the transducer 11. The sensor 8 itself is an elongated rectangular body (see FIG. 4) having a width which is a small fraction of the diameter of a cigarette Z and which is disposed substantially centrally of a row (R1, R2 or R3) of aligned cigarettes Z so that it normally overlies or registers with the end faces EF of successive cigarettes Z of a row when a receptacle 4 containing a group or array 3 of cigarettes advances therealong. In other words, when a row of cigarettes Z advances past a sensor 8, all of the light-emitting fibers direct light against tobacco and all of the light-receiving fibers receive light which is reflected by particles of tobacco at the respective end faces EF of cigarettes Z in the row that advances beyond the detector 9. It goes without saying that the same holds true for the detectors 9 including the sensors 8b1, 8b2 and 8b3 except that certain fibers of sensors in such detectors receive light which is reflected by the filaments or other constituents of successive filter mouthpieces F.

A so-called phantom or pattern 13 is provided on the belt 2 between two neighboring receptacles 4 to cause the detectors including the sensors 8a1 to 8b3 to generate reference signals which are indicative of ideal or desirable tobacco-containing sections T and ideal filter mouthpieces F. The reference signals which are generated by the detectors during travel of the phantom 13 therealong are compared with signals which are generated by the detectors during monitoring of cigarettes Z to ascertain whether or not the quality of tested cigarettes Z is satisfactory for admission of the respective arrays 3 into the cigarette packing machine proper.

The testing station 6 is located upstream of an ejecting station 14, as considered in the direction of travel of the belt 2. Such direction is indicated by the arrow A. The ejecting station 14 accommodates a pusher 16 which is reciprocable transversely of the belt 2 by a motor 17 which receives signals whenever one of the detectors including the sensors 8a1 to 8b3 detects a defective cigarette Z. The motor M which drives the belt 2 of the conveyor 1 is driven intermittently, and the motor 17 is arranged to cause the pusher 16 to perform a working stroke (in the direction of arrow B shown in FIG. 1) during intervals between successive stepwise advances of the receptacles 4. The dimensions of the pusher 16 are selected in such a way that it can expel an entire array 3 of cigarettes Z from the adjacent receptacle 4 when the motor 17 receives a signal denoting that the array 3 of cigarettes Z which are aligned with the pusher 16 contains at least one detective rod-shaped article.

FIG. 1 shows the conveyor 1 in the course of movement through a distance corresponding to that between the centers of two neighboring receptacles 4. Thus, a receptacle 4 advances between the testing units 7a and 7b but the pusher 16 does not register with a receptacle 4, namely, with an array 3 of cigarettes Z. When the conveyor 1 is brought to a halt, the rightmost receptacle 4 of FIG. 1 has been moved beyond the testing station 6 and the receptacle denoted by the reference character 4X is in accurate register with the pusher 16 at the ejecting station 14. The stations 6 and 14 can be said to constitute two spaced-apart portions of the endless path along which the receptacles 4 are transported in stepwise fashion.

The signal processing and evaluating circuit of FIG. 6 comprises six transducers 11a1, 11a2, 11a3, 11b1, 11b2 and 11b3 which transmit signals to the first inputs a of the corresponding adjustable differential amplifiers 18a1, 18a2, 18a3, 18b1, 18b2 and 18b3 as well as to the first inputs a of first adjustable memories 19a1, 19a2, 19a3, 19b1, 19b2 and 19b3. The second inputs b of the memories 19a1 to 19b3 are connected with the output of a pulse generator 27. The outputs of the memories 19a1 to 19b3 are respectively connected with the second inputs b of the associated differential amplifiers 18a1 to 18b3. The pulse generator 27 transmits a signal whenever the phantom 13 advances past the testing station 6. Each amplifier can be said to constitute a signal comparing means.

The outputs of the adjustable differential amplifiers 18a1 to 18b3 are respectively connected with the first inputs a of second adjustable memories 21a1, 21a2, 21a3, 21b1, 21b2 and 21b3. The second inputs b of the memories 21a1, 21a3, 21b1 and 21b3 are connected with a pulse generator 28 which transmits a signal whenever a row R1 and/or R3 begins to advance past the testing station 6. The second inputs b of the memories 21a2 and 21b2 are connected to the output of a further pulse generator 29 which transmits a signal whenever a row R2 begins to advance past the testing station 6. The signal from the pulse generator 29 trails the signal from the pulse generator 28 because the cigarettes Z of the row R2 in each group 3 are staggered with reference to the cigarettes Z in the adjacent outer rows R1 and R3. The pulse generator 28 continues to transmit a signal as long as the rows R1 and R3 of a group 3 advance past the testing station 6. Analogously, the pulse generator 29 continues to transmit a signal as long as a row R2 continues to advance past the station 6. It will be appreciated that the duration of a signal from the pulse generator 29 is shorter than that of a signal from the pulse generator 28 because each row R2 is supposed to contain only six parallel cigarettes Z whereas each of the rows R1, R3 is assumed to contain seven parallel cigarettes Z. The duration of transmission of a signal from the pulse generator 28 is preferably selected in such a way that, while the pulse generator 28 transmits a signal, the sensors 8a1, 8a3, 8b1 and 8b3 overlap in their entirety the adjacent end faces EF of cigarettes Z in the respective rows R1 and R3. Analogously, the duration of each signal which is generated by the pulse generator 29 is preferably selected in such a way that, during transmission of the signal, the sensors 8a2 and 8b2 overlap in their entirety the end faces EF of cigarettes Z in the respective median row R2.

The outputs of the second memories 21a1 to 21b3 are respectively connected with the inputs of associated threshold circuits 22a1, 22a2, 22a3, 22b1, 22b2 and 22b3.

The outputs of the threshold circuits $22a1$ to $22b3$ are connected with the corresponding inputs of an OR gate 23 whose output is connected with the first stage of a time-delay device here shown as a shift register 24 the last stage of which is connected with the input of the motor 17 for the pusher 16 by a suitable amplifier 26. The delay which is effected by the shift register 24 corresponds to the interval of time which is required to move a group or array 3 of cigarettes Z from the testing station 6 to the ejection station 14.

The operation of the apparatus which is shown in FIGS. 1 to 6 is as follows:

The belt 2 of the conveyor 1 advances successive receptacles 4 first past a filling station, such as the magazine of a packing machine wherein a customary plunger or pusher introduces arrays of twenty cigarettes Z into the receptacle 4 which dwells at the filling station during the interval between successive advances of the conveyor. Successive filled receptacles 4 are thereupon advanced past the testing station 6. The phantom 13 moves past the testing station 6 once during each cycle involving the advancement of all receptacles 4 past the station 6, namely, between the testing units $7a$ and $7b$.

One half of the fibers of each of the sensors $8a1$ to $8b3$ continuously emit light which impinges upon the end faces EF of the tobacco-containing sections T and filter mouthpieces F while a receptacle 4 advances past the station 6. The end faces EF of the tobacco-containing sections T and filter mouthpieces F reflect the light into the adjacent end portions of the other half of fibers forming part of the sensors $8a1$ to $8b3$. Such reflection takes place while the cigarettes Z of an array 3 advance between the testing units $7a$ and $7b$ at the station 6.

The reflected signals are transmitted to the respective transducers $11a1$ to $11b3$ which generate corresponding signals and transmit such signals to the first inputs a of the associated signal comparing amplifiers $18a1$ to $18b3$ and first memories $19a1$ to $19b3$. When the phantom 13 advances between the testing units $7a$ and $7b$, the pulse generator 27 transmits a signal to the second inputs b of the first memories $19a1$ to $19b3$ so that the memories $19a1$ to $19b3$ are ready to accept reference signals which are transmitted at such time by the associated transducers $11a1$ to $11b3$, namely, reference signals which are generated by the transducers in response to passage of the phantom 13 between the testing units $7a$ and $7b$. The memories $19a1$ to $19b3$ thereupon store such reference signals for predetermined intervals of time, namely, until the phantom 13 returns into the space between the units $7a$, $7b$ and causes the pulse generator 27 to transmit another signal enabling the first memories $19a1$ to $19b3$ to accept reference signals from the associated transducers $11a1$ to $11b3$.

The signal at the output of the amplifier $18a1$ corresponds to the difference between the intensities of signals transmitted by the output of the transducer $11a1$ and the output of the associated first memory $19a1$. In other words, the intensity of signal at the output of the amplifier $18a1$ denotes the extent to which the quality of cigarettes Z (and more particularly of the tobacco rod sections T in a row $Ra1$) deviates from the optimum quality as indicated by the reference signal which is initiated by the phantom 13. The signal which appears at the output of the amplifier $18a1$ is transmitted to the first input a of the second memory $21a1$ while the second input b of the memory $21a1$ receives a signal from the pulse generator 28, namely, while a row R1 of cigarettes Z advances past the testing unit $7a$. As explained above, the signal at the output of the amplifier $18a1$ denotes the difference between the intensities of signals transmitted by the transducer $11a1$ and memory $19a1$. Such signal is transmitted to the threshold circuit $22a1$ which transmits a signal to the corresponding input of the OR gate 23 when the intensity of the signal furnished by the memory $21a1$ exceeds a preselected value. This is the case when a cigarette Z of the row R1 is missing, when the tobacco-containing end of a cigarette Z in the row R1 is improperly filled with tobacco particles or (in the case of filter mouthpieces F) when a mouthpiece F is missing. The duration of signals which are transmitted by the output of the threshold circuit $22a1$ is relatively short. Such signals are transmitted to the first stage of the shift register 24 which delays the signals until the corresponding arrays 3 reach the ejecting station 14. At such time, the amplifier 26 amplifies the signal which is transmitted by the last stage of the shift register 24 and applies it to the input of the motor 17 which causes the pusher 16 to expel the corresponding array 3 from the path on the conveyor 2. The container into which the unsatisfactory cigarettes Z are expelled is not specifically shown in the drawing.

The operation of the other five components of the evaluating circuit FIG. 6 is analogous. Thus, the threshold circuit $22a2$ receives signals which denote the difference between the signals transmitted by the transducer $11a2$ and the reference signal transmitted by the associated first memory $19a2$. The threshold circuit $22a3$ transmits signals when the difference between the intensities of signals generated by the transducer $11a3$ and the associated memory $19a3$ is excessive, and so forth.

Detectors which are capable of being used in the testing units $7a$ and $7b$ are disclosed, for example, in the article entitled "The role of fiber optics in photoelectric sensing applications" by Robert W. Fayfield which is published in The Banner Catalog for Photoelectrics (pages 1 to 9). The distance between the rectangular outlines of sensors $8a1$ to $8b3$ at the station 6 and the respective end faces EF of articles Z during testing is preferably between 2 and 5 mm; the power supply may be a source of 24 volt direct current; and the power consumption of the illustrated apparatus is in the range of 100 milliamperes. It has been found that the resolution of the detectors 9 is very high due to the fact that the sensors $8a1$ to $8b3$ have a rectangular outline at the testing station 6.

It is clear that the testing unit $7a$ or $7b$ can be replaced by any other suitable testing device, i.e., that it suffices if the unit $7a$ or $7b$ is assembled of detectors of the type shown in FIG. 5. Furthermore, the improved method and apparatus can be resorted to for testing of simpler groups or arrays of rod-shaped articles which constitute or form part of smokers' products. Thus, each group or array can have two rows of ten or five articles each, or each array can consist of a single row of e.g., four or five parallel rod-shaped articles. This entails a corresponding simplification of the evaluating circuit which processes the signals furnished by the transducer or transducers 11 or by analogous signal generating means which is or are capable of converting the reflected light into signals denoting the characteristics, the presence or the absence of articles in the respective row or rows.

A packing machine wherein the improved apparatus can be put to use is disclosed, for example, in commonly owned U.S. Pat. No. 3,805,477 granted Apr. 23, 1974 to Kruse et al. FIG. 2 of this apparatus shows a conveyor 5011 which can be used as a substitute for the conveyor 1 shown in FIGS. 1 to 3 of the present application.

When the improved apparatus is in use, its component parts (or at least some of its component parts) are progressively contaminated by tobacco dust which is invariably present in cigarette making and analogous plants, by other types of dust particles and/or by a combination of such contaminants. While the contaminants need not influence the operation of all components which are exposed thereto (i.e., on which the contaminants settle), certain components of the testing apparatus are likely to adversely influence the accuracy of the testing operation as their contamination progresses. Typical examples of such components are lenses, mirrors, glass panes and/or analogous optical elements which are placed across the path of light that issues from the sources 10 as well as across the path of light that is reflected by the end faces EF of the articles Z being tested. FIG. 7 shows a first optical element $L_1$ which is placed in front of the transducers $11a1$ to $11a3$ (e.g., into the space between the receptacle 4 shown in FIG. 3 and the left-hand testing unit $7a$), and a second optical element $L_2$ which is placed in front of the transducers $11b1$ to $11b3$ (e.g., into the space between the receptacle 4 of FIG. 3 and the right-hand testing unit $7b$). If desired, each of the optical elements $L_1$ and $L_2$ can be composed of several discrete lenses, panes or mirrors, i.e., one for each of the transducers $11a1$ to $11b3$.

Particles of tobacco dust or the like which settle on the optical element $L_1$ and/or $L_2$ are likely to distort the signals which are generated during transport of cigarettes Z and/or phantom or pattern 13 through the testing station 6. To this end, the evaluating circuit of FIG. 6 preferably further comprises the structure or arrangement which is shown in FIG. 7. Such arrangement includes a first amplifier $30a$ whose input a receives signals from the output of at least one of the transducers $11a1$ to $11a3$ forming part of the testing unit $7a$. FIG. 7 shows that the amplifier $30a$ is connected with the output of the transducer $11a1$. The second input b of the amplifier $30a$ is connected with the pulse generator 27 in order to ensure that the amplifier $30a$ accepts a signal from the transducer $11a1$ only when the pattern 13 advances past the testing station 6. The output of the amplifier $30a$ transmits signals to the gain adjustment inputs c of the amplifiers $18a1$, $18a2$ and $18a3$, and such signals are indicative of a reduction of intensity of successive signals which are generated by the transducer $11a1$ during successive passes of the pattern 13 therealong. Thus, the amplification factors of the amplifiers $18a1$ to $18a3$ are adjusted to compensate for progressing contamination of the optical element $L_1$ and to thus eliminate, or at least reduce, the deleterious effects of contaminants upon the testing operation, namely, upon the testing of tobacco-containing ends of the cigarettes Z. The output of the amplifier $30a$ further transmits signals to an amplifier $31a$ which compares such signals with a reference signal transmitted by a suitable source $32a$, e.g., an adjustable potentiometer. When the intensity or another characteristic of the signal which the amplifier $31a$ receives from the amplifier $30a$ is less than the minimum acceptable value (as indicated by the reference signal from the source $32a$), the output of the amplifier $31a$ transmits a signal to the input of a flip-flop 33 or an analogous control circuit which initiates stoppage of the entire packing machine (including the conveyor belt 2) by way of a transistor 34, a relay 35 and a switch 36. This takes place when the optical element $L_1$ is contaminated to such an extent that the ability of amplifiers $18a1$ to $18a3$ to intensify their output signals in order to compensate for progressing contamination of the element $L_1$ is exhausted. The flip-flop 33 has a reset input d which can receive a signal in response to actuation of a manually or otherwise operable starter switch 37 in order to restart the packing machine and the motor M for the conveyor belt 2.

The output of the transducer $11b1$ in the testing unit $7b$ is connected with the input a of an amplifier $30b$ whose input b is connected with the pulse generator 27 to transmit signals in response to each passage of the pattern or phantom 13 past the testing station 6. Such signals are indicative of the extent of contamination of the optical element $L_2$ and are transmitted to the gain adjustment inputs c of the amplifiers $18b1$, $18b2$ and $18b3$ for the purpose of ensuring that the intensity and/or another characteristic of signals at the outputs of the amplifiers $18b1$–$18b3$ is corrected to account for contamination of the element $L_2$ by tobacco dust and/or other contaminants. The output of the amplifier $30b$ further transmits a signal to the corresponding input of an amplifier $31b$ which receives reference signals from an adjustable potentiometer $32b$ or another suitable source. Such reference signals are indicative of the lower limit of acceptability of signals at the output of the amplifier $30b$. If such limit is exceeded, i.e., if the intensity of a signal at the output of the amplifier $30b$ is less pronounced than that of the reference signal furnished by the source $32b$, the output of the amplifier $31b$ transmits a signal to the flip-flop 33 which arrests the packing machine in the same way as in response to signals from the output of the amplifier $31a$. The flip-flop 33 is reset by the starter switch 37 when the optical element $L_1$ and/or $L_2$ is relieved of tobacco dust and/or other contaminants so that the testing apparatus is again in a condition to properly test the ends of cigarettes Z in successive groups 3. It is clear that the signals at the output of the amplifier $31a$ and/or $31b$ can also be transmitted to a single signal generator or to two discrete signal generators serving to transmit visible, audible and/or otherwise detectable signals for the convenience of attendants.

If desired, the structure which is shown in FIG. 7 can be modified or amplified by the provision of rotary, oscillatable or otherwise movable wipers $W_1$ and $W_2$ which are designed to automatically clean the optical elements $L_1$ and $L_2$ (i.e., to relieve such elements of contaminants which have settled thereon) in response to signals from the relay 35, from the output of the amplifier $31a$ or from the output of the amplifier $31b$. FIG. 7 shows a motor 38 which serves to actuate the wipers $W_1$ and $W_2$ whenever the relay 35 is energized or deenergized to open the switch 36. A discrete motor 38 can be provided for each of the two wipers $W_1$ and $W_2$; one of these motors is then actuated in response to transmission of a signal by the amplifier $31a$ and the other of these motors is started when the amplifier $31b$ transmits a signal to the flip-flop 33. If the testing apparatus embodies the wipers $W_1$, $W_2$ and the motor 38, the switch 36 can constitute an optional feature because the amplifiers $31a$, $31b$ can be readily adjusted to transmit signals shortly prior to excessive contamination of the elements $L_1$ and $L_2$. Thus, these elements can be relieved of contaminants in good time before the amplifiers $18a1$ to $18b3$ reach the limit of their adjustability.

An advantage of the arrangement which is shown in FIG. 7 is that it automatically compensates for contamination of the testing apparatus when the latter is in use and that it can automatically interrupt the making and/or processing of articles to be tested when the contamination is excessive, i.e., when the limit of adjustability of the amplifiers 18a1 to 18b3 is exceeded. These amplifiers can be said to constitute means for modifying the signals which are transmitted to the memories 21a1 to 21b3 as a function of detected contamination of one or more selected elements or components of the testing apparatus. The contamination detecting means are the parts 30a, 31a, 32a and 30b, 31b, 32b.

It is clear that the apparatus can be equipped with an arrangement which monitors the contamination of only one of the optical elements $L_1$ and $L_2$, e.g., the contamination of the optical element $L_1$ which is adjacent to the tobacco-containing ends of the cigarettes travelling along the path defined by the conveyor belt 2. It is then assumed that the contamination of the optical element $L_2$ progresses at the same rate as that of the element $L_1$. It is further clear that the arrangement of FIG. 7 can be replaced with a more sophisticated arrangement having six discrete sections, one for each of the transducers 11a1 to 11b3. This depends on the conditions prevailing in the plant where the improved testing apparatus is put to use.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. Apparatus for testing cigarettes or analogous rod-shaped articles of predetermined diameter which constitute or form part of smoker's products, comprising conveyor means arranged to transport successive groups, each consisting of at least one row of parallel articles, sideways along a predetermined path; testing means adjacent to a predetermined portion of said path and including a testing device comprising at least one detector having a light source, a transducer, and a sensor disposed substantially centrally of the row of parallel articles and having fiber optics arranged to convey light from said source against one end face of each successive article in the rows of successive groups, whereby such end faces reflect light and the extent of light reflection is indicative of the condition, presence or absence of the respective articles, and to convey reflected light to said transducer whereby the latter generates signals denoting the extent of light reflection, said sensor having a substantially rectangular outline in the region of said portion of said path and such outline being formed in part by fibers which supply light and in part of fibers which convey reflected light, one dimension of said outline being a small fraction of said predetermined diameter; and means for processing those signals which are generated during transport of successive groups along said portion of said path.

2. The apparatus of claim 1, wherein said processing means comprises means for furnishing a reference signal denoting the desired extent of light reflection by the end faces of articles, means for comparing successive signals generated by said transducer with said reference signal, and means for generating additional signals when the difference between a signal from said transducer and said reference signal exceeds a preselected value.

3. The apparatus of claim 2, further comprising means for ejecting from said path those rows wherein an article has initiated the generation of an additional signal.

4. The apparatus of claim 1, wherein the length of said sensor, as considered in the direction of transport of groups of articles along said path, exceeds said predetermined diameter.

5. The apparatus of claim 1, wherein said transducer is arranged to generate a continuous signal for each row of articles.

6. The apparatus of claim 1, wherein each group comprises several rows of parallel articles and said testing device includes a discrete detector for each row of a group.

7. The apparatus of claim 1, wherein said testing means includes a second testing device adjacent to said path, said testing devices being disposed at the opposite sides of said path and the detectors of said testing devices being arranged to monitor the respective end faces of articles in successive rows advancing past said testing devices.

8. The apparatus of claim 1, further comprising means for driving said conveyor means in stepwise fashion.

9. The apparatus of claim 1, wherein said path is an endless path and said conveyor means comprises a pattern arranged to effect the generation by said transducer of reference signals denoting desirable characteristics of articles when said pattern is transported along said portion of said path.

10. The apparatus of claim 9, wherein said processing means comprises a first memory arranged to store a reference signal during each interval of transport of said pattern from and back to said portion of said path, signal comparing means having a first input connected with said transducer, a second input connected with said memory and an output arranged to transmit further signals denoting the differences between said reference signal and signals transmitted by said transducer, a second memory arranged to receive further signals while a row of articles is transported along said portion of said path, and a threshold circuit arranged to receive signals from said second memory and to generate an additional signal when the intensity of signal from said second memory exceeds a predetermined value.

11. The apparatus of claim 10, further comprising means for delaying each additional signal for an interval of time corresponding to that which elapses during transport of a row an article of which has caused the generation of an additional signal from said predetermined portion to a second predetermined portion of said path.

12. The apparatus of claim 1, further comprising at least one element which is installed in the path of light between said source and said transducer and is subject to contamination when the apparatus is in use, such as by tobacco dust, said signal processing means including detecting means arranged to generate second signals denoting the extent of contamination of said element and means for modifying said first mentioned signals as a function of the intensity of said second signals.

13. The apparatus of claim 12, wherein said element is a light-transmitting element.

14. The apparatus of claim 12, wherein said detecting means includes means for comparing said second signals with a reference signal denoting maximum permissible contamination of said element and further comprising means for arresting said cohveyor means when the contamination of said element matches said maximum permissible value.

15. The apparatus of claim 12, wherein said modifying means comprises at least one adjustable amplifier for said first mentioned signals.

16. The apparatus of claim 12, further comprising means for automatically relieving said element of contaminants when the characteristics of said second signals are indicative of excessive contamination of said element.

17. A method of testing cigarettes or analogous rod-shaped articles which constitute or form part of smokers' products, comprising the steps of transporting successive groups, each consisting of at least one row of parallel articles, sideways along a predetermined path; testing successive articles of successive rows in a predetermined portion of said path, including establishing a light source, directing from said light source a plurality of light beams along discrete optical paths against the central region of one end face of each article of a row, as considered in the longitudinal direction of the row, in said portion of said path so that the one end face reflects the beams and the extent of such reflection is indicative of the condition, presence or absence of articles, and utilizing the reflected light for continuous generation of signals denoting the extent of light reflection by a full row of articles; and processing said signals.

18. The method of claim 17, wherein said processing step comprises comparing said signals with a reference signal denoting the desired light reflectivity of the end faces of articles and ejecting from said path those rows wherein the testing of articles has resulted in the generation of signals deviating excessively from said reference signal.

19. The method of claim 17, further comprising the step of simultaneously testing the second end face of each successive article in each row.

20. The method of claim 17, wherein each group contains several rows of parallel articles and said testing step includes testing the end faces of all articles in a group at one side of said path during transport of groups along said portion of said path.

21. The method of claim 17 of testing smokers' products in an environment wherein said optical paths are subject to progressing contamination by particles of dust or the like, further comprising the steps of monitoring said paths, generating second signals denoting the extent of contamination of said paths, and modifying said first mentioned signals as a function of said second signals.

22. The method of claim 21, further comprising the steps of comparing said second signals with a reference signal denoting the maximum permissible contamination of said paths, and interrupting said transporting step when said second signals are indicative of such maximum permissible contamination.

23. The method of claim 21, further comprising the steps of comparing said second signals with a reference signal denoting the maximum permissible contamination of said paths, and automatically removing contaminants from said paths when said second signals are indicative of such maximum permissible contamination.

* * * * *